United States Patent [19]

McGredy

[11] Patent Number: Plant 5,429

[45] Date of Patent: Apr. 2, 1985

[54] ROSE PLANT 'MACWAIKE'

[76] Inventor: Samuel D. McGredy, 130 B Beach Rd., Castor Bay, Auckland 9, New Zealand

[21] Appl. No.: 518,100

[22] Filed: Jul. 28, 1983

[51] Int. Cl.[3] ..... A01H 5/00

[52] U.S. Cl. ..... Plt./26

[58] Field of Search ..... Plt./22, 26

*Primary Examiner*—James R. Feyrer

*Attorney, Agent, or Firm*—Vincent G. Gioia

[57] ABSTRACT

A new floribunda rose variety with multi-colored flowers combining azalea pink and orient pink.

1 Drawing Figure

The present invention relates to a new and distinct variety of rose plant of the floribunda rose class, which was originated by my crossing as seed parent the rose known as "Tony Jacklin" and as pollen parent the rose known as "Young Quinn". The denomination of the new rose is "Macwaihe".

Among the novel characteristics possessed by this new variety which distinguish it from its parents and all other varieties of which I am aware are flowers of unusual multi-coloring borne in large sprays of excellent floribunda inflorescence. Flowers are a combination of azalea pink and orient pink. The flower's unique coloring is highlighted by the good floribunda inflorescence form borne on a disease resistant plant of excellent vigor and quick to repeat. Asexual reproduction by budding of the new variety as performed in Kern County, Calif., shows that the foregoing and other distinguishing characteristics come true to form and are established and transmitted through succeeding propagations.

The accompanying drawing shows typical specimens of the vegetative growth and flowers of the new variety in different stages of development and as depicted in color as nearly true as it is reasonably possible to make the same in a color illustration of this character.

The following is a detailed description of my new variety, with color terminology in accordance with The Royal Horticultural Society Colour Chart (R.H.S.C.C.). The terminology used in color description herein refers to plate numbers in the aforementioned color chart, e.g., "38A" is plate 38A of The Royal Horticultural Society Colour Chart.

Parentage: Seedling.

*Seed parent.*—"Tony Jacklin".

*Pollen parent.*—"Young Quinn".

Class: Floribunda.

The following observations are made of specimens grown outdoors in Kern County, Calif., during the month of June.

FLOWER

Blooming habit: Continuous.

Bud:

(1) *Size.*—Small, 3 to 4 cm.

(2) *Form.*—Long pointed.

(3) *Color.*—When sepals first divide — near 37A becoming quickly near 38A, azalea pink, with bud petal undersurface near 36B.

(4) *Sepals.*—Longer than bud, simple but acuminate.

(5) *Peduncle.*—Length — short. Aspect — straight. Strength — strong, erect. Color — near 143C.

Bloom:

(1) *Size.*—Average size when fully expanded — about 5 cm.

(2) *Borne.*—In medium size sprays, 5–9 flowers.

(3) *Form.*—Sprays are of excellent inflorescence and good floribunda form, laterals all comparable (i.e., no single blooms and no trusses). Individual blooms are initially high centered then reflex.

(4) *Petalage.*—Number of petals under normal conditions — about 30.

(5) *Color.*—Flower buds which start as near 37A and become azalea pink with orient pink reverse open into azalea pink flowers continuing the orient pink reverse. However, individual petals have color shading, for example, on petal top surface, from azalea pink (near 38A) at edge lightening to orient pink, near 36D, toward point of petal attachment. The point of petal attachment is actually near 13B. Inner petal at flower centers when bunched suggest deeper toned azalea pink. At the petal undersurface the orient pink appears in different shades. The petal edges tend to vary with some quite uneven and deeper toned.

Petals:

(1) *Texture.*—Thick.

(2) *Appearance.*—Smooth with satiny sheen.

(3) *Form.*—Broad, oval.

(4) *Arrangement.*—Imbricate.

(5) *Petaloids in center.*—Many.

(6) *Persistence.*—Drop off cleanly.

(7) *Fragrance.*—Slight, spicey.

(8) *Lasting quality.*—Excellent on plant and as cut flower.

REPRODUCTIVE ORGANS

Stamens, filaments and anthers:

(1) *Arrangement.*—Stamens regular, arranged around styles, uneven length, incurved.

(2) *Color.*—Filaments near 14A, anthers near 14C.

Pollen:

*Color.*—Near 14A.

Styles: Long thin, strigose, color near 55B.

Stigmas:

*Color.*—Near 12A.

Hips:

*Shape.*—Ovoid, but rare.

*Size.*—Small.

*Color.*—Near 168D.

*Do seeds protrude?.*—No.

PLANT

Form: Upright, bushy.

Growth: Vigorous, uniform clusters.

*Height attained.*—About 75 cm.

Foliage: Compound 5 to 7 leaflets.

(1) *Size.*—Medium.

(2) *Quantity.*—Abundant with short internodes.

(3) *Color.*—New foliage: Upper side — near 178A. Under side — near 185B. Old foliage: Upper side — near 137B. Under side — near 138C.

(4) *Shape.*—Oval, acuminate.

(5) *Texture.*—Upper side is glossy and under side is glaborous.

(6) *Edge.*—Serrate.

(7) *Serration.*—Simple.

(8) *Leaf stem.*—Color — near 145A. Under side — near 145B.

(9) *Stipules.*—Simple.

(10) *Resistance to disease.*—Blackspot — excellent. Mildew — excellent. Rust — excellent.

Wood:

(1) *New wood.*—Color — near 70B. Bark — smooth.

(2) *Old wood.*—Color — near 138B. Bark — smooth.

Thorns:

(1) *Thorns.*—Quantity (main stalk): few. On laterals from stalk — few. Form — long, pointed. Length — small. Color — near 145A. Position — irregular.

(2) *Prickles.*—Few to none on stem, profuse on laterals.

Winter hardiness: Needs ordinary winter protection.

I claim:

1. A new and distinct variety of rose plant of the floribunda class, substantially as shown and described, characterized particularly by excellent floribunda inflorescence with laterals all comparable, flowers of unusual azalea pink and orient pink coloring, vigorous plant of excellent disease resistance, and quick repeating flowering habit.

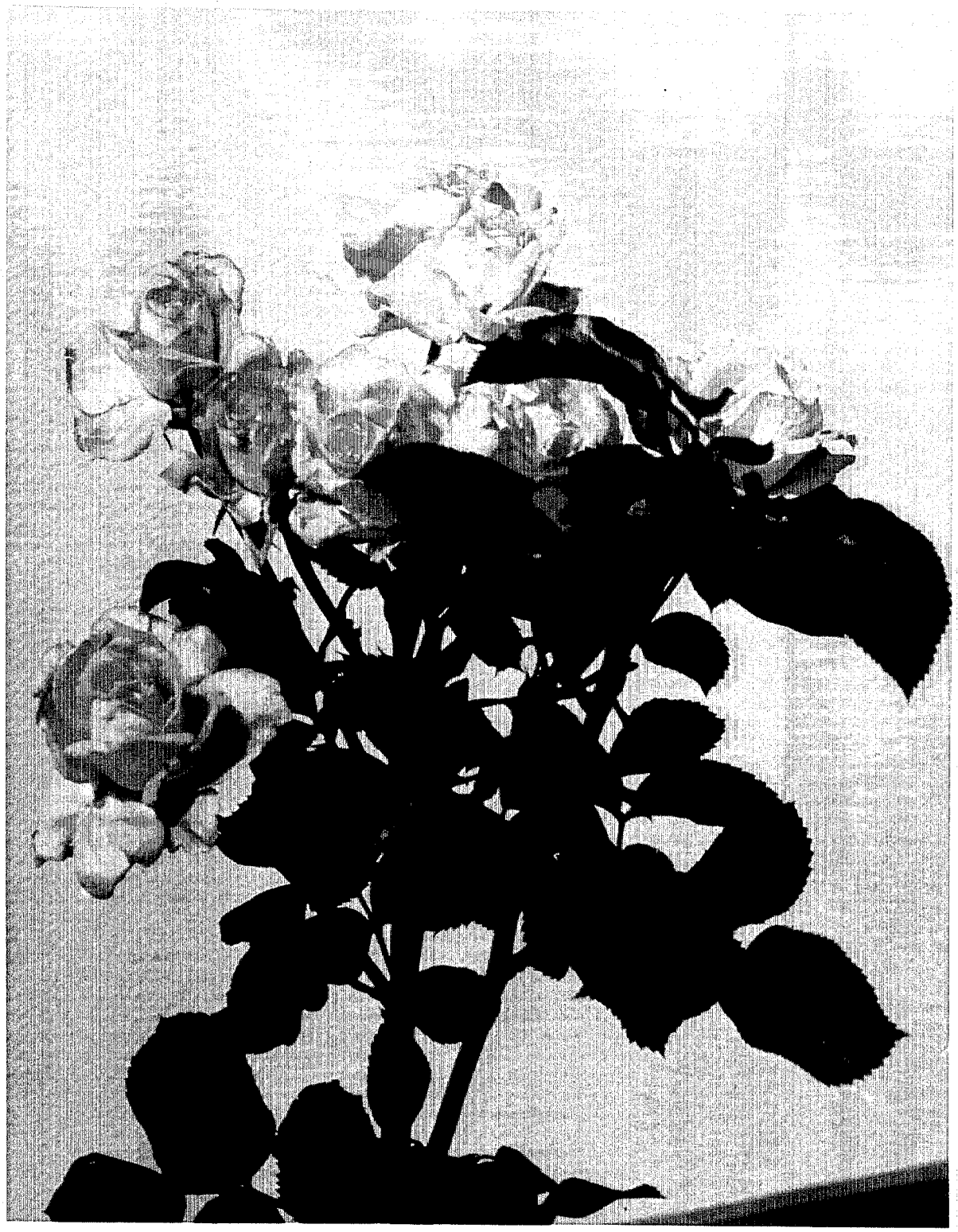

* * * * *